United States Patent [19]
Perry et al.

[11] 3,965,129
[45] June 22, 1976

[54] OPTICAL RESOLUTION OF ORGANIC CARBOXYLIC ACIDS

[75] Inventors: Clark William Perry, Saddle River; Sidney Teitel, Clifton, both of N.J.

[73] Assignee: Hoffmann-La Roche Inc., Nutley, N.J.

[22] Filed: May 15, 1975

[21] Appl. No.: 577,806

Related U.S. Application Data

[62] Division of Ser. No. 404,951, Oct. 10, 1973, Pat. No. 3,901,915.

[52] U.S. Cl. .......................................... 260/348 A
[51] Int. Cl.² ...................................... G07D 303/38

[58] Field of Search ............................. 260/348 A

[56] References Cited
UNITED STATES PATENTS 3,810,931   5/1974   Cuthrie et al. .................. 260/348 A

*Primary Examiner*—Norma S. Milestone
*Attorney, Agent, or Firm*—Samuel L. Welt; George M. Gould; Raymond R. Wittekind

[57] ABSTRACT

Racemic organic carboxylic acids are efficiently resolved into their enantiomers with antipodes of α-methyl-p-nitrobenzylamine.

1 Claim, No Drawings

OPTICAL RESOLUTION OF ORGANIC CARBOXYLIC ACIDS

This is a division of application Ser. No. 404,951 filed Oct. 10, 1973, now U.S. Pat. No. 3,901,915, issued Aug. 26, 1975.

BACKGROUND OF THE INVENTION

It is well known that many natural products contain one or more asymmetric centers and thus can occur in optically active forms. As a rule, one optical form predominates in nature, and only this optical isomer is responsible for the particular properties of the compound such as taste, odor, toxicity and pharmacological properties. This generally applies as well to synthetic compounds, particularly in the medicinal or pharmaceutical field. That is, one optical antipode usually exhibits the desired biological activity, whereas the other does not or does to a much smaller extent or, in fact, may even exhibit undesirable properties.

It has become accepted procedure in the synthesis of biologically active molecules to prepare the desired molecule in optically active form. While, in some cases, this may be accomplished utilizing enzymatic or fermentation techniques, a chemical optical resolution is the only method which can usually be used on a technical scale. For convenience, resolution is usually performed at a stage in which the intermediate or final product has a functional group which is suited for the resolution process, usually an amine or carboxylic acid group. The racemic compound to be resolved is reacted with an optically pure compound having a complementary functional group to form mixtures of diastereomeric compounds, usually salts, which may then be separated due to their differences in physical properties. Usually fractional crystallization is employed. Compounds having a carboxylic acid group are commonly resolved by reaction with an optically active amine, and compounds possessing an amine group may be resolved by reaction with an optically active acid, for example, an optically active carboxylic or sulfonic acid.

In the past, the resolution of racemates having carboxylic acid groups was accomplished utilizing optically active amines derived from natural sources, most notably the alkaloids such as brucine, strychnine, cinchonidine, and so forth. The use of these compounds presents many disadvantages such as toxicity, questionable optical purity, availability (inasmuch as they must be obtained from natural sources), and the fact that they normally occur in nature in only one optical form so that only one antipode is available for a potential resolution problem.

In recent years, the use of simpler synthetic organic amine resolving agents has become wide-spread. In particular, amines that have been used extensively for optical resolution are antipodes of α-methylbenzylamine (α-phenylethylamine) and simple derivatives thereof, such as N- and N,N-lower alkyl derivatives; as well as antipodes of α-naphthylethylamine. While these amines have been used extensively, there are many instances in which resolution does not occur either through the lack of formation of crystalline salts or the fact that the diastereomeric salts formed, even if crystalline, often do not differ sufficiently in physical properties to allow facile separation.

Hence, it would be desirable to have available optically active amine resolving agents which are easily prepared, are simple to use, provide highly crystalline salts, and which will resolve a wide range of racemic acids of varying structure and type.

Both optical antipodes of α-methyl-p-nitrobenzylamine p-nitrobenzylamine have been previously described in the literature. See for example, Cope, et al., Journal of the American Chemical Society, Vol. 92, page 1243 (1970). The antipodes of this compound have been used, as complexes with platinum, for the partial resolution of a cylic allene, notably 1,2-cyclononadiene. However, there was no suggestion to use such compounds for the resolution of organic carboxylic acids.

DETAILED DESCRIPTION OF THE INVENTION

The present invention relates to a method of resolving racemic organic carboxylic acids into their respective enantiomers by the use of an optical antipode of α-methyl-p-nitrobenzylamine. The two antipodes of α-methyl-p-nitrobenzylamine are hereinafter referred to as the R-(+) and the S-(−) antipodes. These materials are prepared in a number of fashions as described in the literature, most commonly by nitration of the corresponding antipode of α-methylbenzylamine, usually after protection of the amino group.

The type of acids which may be resolved by use of one or the other of the aforementioned antipodes of α-methyl-p-nitrobenzylamine are racemic organic carboxylic acids. These acids may contain more than one carboxyl group. There may also be present in the molecule being resolved any number of functional groups such as epoxide moieties, lactones, double or triple bonds, aromatic rings, including heterocyclic aromatic systems, carbonyl groups, hydroxy groups, amide groups, halogen groups, alkoxy groups, and so forth.

Acids which are particularly preferred for use in the present resolution process are racemic threo-epoxyaconitic acid (I), racemic threo-hydroxycitric acid, γ-lactone (racemic Garcinia acid lactone) (II), and racemic N-lower alkanoyl or N-benzoyl-6-chlorotryptophans, preferably racemic N-formyl-6-chlorotryptophan (III). The structures for these acids are presented below.

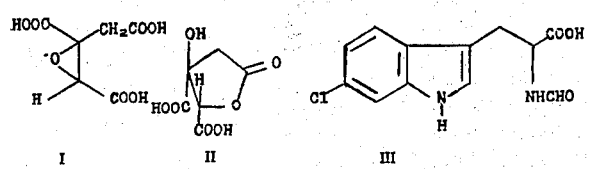

The (+)-antipode of I is useful for the control of lipogenesis and also serves as an intermediate for the preparation of the γ-lactone of (−)-hydroxycitric acid (II) and (−)-hydroxycitric acid itself, both of which are useful lipogenic control agents. Reference to the utility of these compounds may be found in U.S. pat. application, Ser. No. 204,334, Guthrie, et al., now U.S. Pat. No. 3,810,931 and U.S. Pat. 3,764,692, respectively. N-formyl-6-chlorotryptophan (III) can be converted to 6-chlorotryptophan, the D-antipode of which is useful as a non-nutritive sweetening agent. See, for example, German Offenlegungsschrift 1,917,844 (C.A. 72:

30438 c) and South African Patent 69/102,303 (C.A. 75: 62341u).

Optical resolution using the present resolving agents is accomplished in the standard manner for optical resolutions. Generally, this involves contacting the racemic acid to be resolved with one of the antipodes of α-methyl-p-nitrobenzylamine in an inert solvent medium. The amount of resolving agent which may be utilized can vary greatly depending upon the particular acid being resolved, the number of carboxyl groups per molecule of acid being resolved, and so forth. Generally, one will utilize between about 0.4 and about 10 moles of resolving agent for each mole of racemic acid being resolved. A particularly preferred quantity of resolving agent is in the range of from about 0.5 to about 2.0 moles of resolving agent for each mole of racemic acid.

Inert solvent media that may be utilized for the present resolution process include lower alkanols such as methanol, ethanol, 1-propanol, 2-propanol, 1-butanol, and so forth; lower alkyl ketones such as acetone, methyl ethyl ketone, diethyl ketone, and so forth; ethers such as diethyl ether, tetrahydrofuran, isopropyl ether, dioxane and so forth; aliphatic hydrocarbons, such as n-pentane, n-hexane, cyclohexane, and so forth; aromatic hydrocarbons such as benzene, toluene, xylene, and so forth; esters such as ethyl acetate, propyl acetate, ethyl propionate, and so forth; nitriles such as acetonitrile; mixtures of the above; and mixtures of the above mentioned wafer-miscible solvents with water. Particularly preferred solvents for the present resolution are lower alkanols such as methanol and ethanol, lower alkyl ketones such as acetone, and mixtures of these with water.

Upon treatment of the racemic acid with the optically active amine, there is formed a mixture of diastereomeric salts. These salts have different physical properties and may be separated by various physical means well known to one skilled in the resolution art. Such means include, for example, fractional crystallization, selective extraction, and so forth. A particularly preferred method for separation of the diastereomeric salts is fractional crystallization. When employing fractional crystallization as a separation method, one will adjust the solvent and concentration such that, upon formation of the diastereomeric salt, some of the salt will precipitate from the solvent media, leaving the remainder in solution. Generally, the precipitated material is enriched in one of the diastereomeric salts and, of course, the filtrate or mother liquor is similarly enriched in the other isomer. Upon further crystallization of the precipitated salt, if necessary, this salt is brought to purity, that is, it will be the salt of only one of the antipodes of the organic acid. Purity of the salt is generally recognized when its properties, such as melting point and optical rotation, do not change upon further crystallization. Alternatively, if a sample of the pure optically active acid is available, it may be converted to optically pure salt for comparison purposes.

The optically pure salt may then be decomposed to afford the pure carboxylic acid or, alternatively, the salt may be used directly for subsequent chemical conversions. In general, decomposition of the salt is effected either by treatment with a strong acid or with a strong base, that is, an acid stronger than that which is being resolved, or a base stronger than the α-methyl-p-nitrobenzylamine. Displacement with an acid generally employs a mineral acid, such as hydrochloric acid or sulfuric acid. In such a case, there would be obtained the free resolved carboxylic acid as well as the salt of the α-methyl-p-nitrobenzylamine with the particular acid used for the displacement. If a strong base, such as, for example, an alkali metal hydroxide, e.g., sodium hydroxide, is used for the displacement, there would be obtained the salt of the resolved carboxylic acid, for example, the sodium salt, as well as the free α-methyl-p-nitrobenzylamine. In either case, after decomposition of the salt, the materials are easily separated due to their differences in physical properties, particularly solubility in organic or aqueous media.

A particularly preferred method for decomposition of salts of carboxylic acids with α-methyl-p-nitrobenzylamine involves treatment with a mineral acid such as hydrochloric acid.

The mineral acid salt of the optically active α-metgyl-p-nitrobenzylamine, upon further treatment with base, affords the free amine which may then be extracted into organic media allowing a high recovery of the resolving agent without loss of optical purity. Thus, recycling of the resolving agent is accomplished in an efficient manner making the use of such resolving agents highly economical.

Alternatively, the pure diastereomeric salt may be directly converted by other chemical reactions to different compounds. For example, the α-methyl-p-nitrobenzylamine salt of (+)-threo-epoxyaconitic acid may be directly converted to the γ-lactone of (−)-hydroxycitric acid by opening of the epoxide and lactonization.

The particular salts which are formed during the resolution process will vary depending upon the carboxylic acid employed. Thus, if one utilizes a carboxylic acid having two or more carboxylic acid groups, there may be obtained a mono-, di-, tri-, etc. salt of the carboxylic acid with the amine. Of course, the particular salt which may be formed will also depend upon the quantity of resolving agent utilized.

For example, in the resolution of racemic threo-epoxyaconitic acid utilizing approximately 1.8 moles of resolving agent for each mole of carboxylic acid, there is obtained a high yield of a salt containing two moles of amine for each mole of carboxylic acid, that is, two of the three available carboxyl groups are involved in salt formation. In the resolution of racemic threohydroxycitric acid, γ-lactone with approximately 1.25 moles of resolving agents for each mole of acid, there is obtained a salt which contains two moles of amine for each mole of acid.

It is noteworthy that the use of α-methyl-p-nitrobenzylamine antipodes as resolving agents leads to the formation of very highly crystalline salts which are easily separated by fractional crystallization and thus allows a highly efficient optical resolution of carboxylic acids. In fact, in many cases, the use of α-methyl-p-nitrobenzylamine leads to the formation of highly crystalline salts, whereas the use of the parent compound, i.e. α-methylbenzylamine itself, does not lead to the formation of any crystalline salt, thus being impractical for optical resolution. This surprising and unpredictable phenomenon is of extreme importance for the resolution of racemic compounds. Thus, for example, for the resolution of threo-epoxyaconitic acid, threohydroxycitric acid, γ-lactone and N-formyl-6-chlorotryptophan, no crystalline salt could be obtained utilizing antipodes of α-methylbenzylamine as potential resolving agents, whereas high yields of highly crystalline salts, which were easily purified to afford the desired diastereomeric salt, were obtained when an antipode of α-methyl-p-nitrobenzylamine was employed.

Specific examples of the use of antipodes of α-methyl-p-nitrobenzylamine for optical resolution of organic carboxylic acid are presented below. These examples are illustrative only of the invention and are not to be construed as limitative thereof in any manner.

EXAMPLE 1

100.0 g (0.826 mole) of R-(+)α-methylbenzylamine was added with vigorous stirring to 230 ml of acetic anhydride over a period of ½ hr, during which time the temperature rose to about 85°. The solution was heated to reflux for 2 hrs, cooled, and concentrated to a viscous oil under reduced pressure. 250 ml of ice water was added to the residue and the mixture was stirred vigorously for 1 hr. The solid product was collected by filtration, washed thoroughly with water, and pressed as dry as possible.

The damp solid, N-acetyl derivative, was added in small portions to 650 ml of 90% nitric acid at −8° to −12° over a period of 30 mins, using a dry ice-acetone bath to control the temperature, which was maintained at −8° to −12° for an additional hour. The mixture was poured into 1800 ml of ice water and the pH was adjusted to 2.0 with 50% sodium hydroxide solution (approximately 1 liter) while stirring and cooling with a dry ice-acetone bath to keep the temperature below 40°. The mixture was extracted with three 1.1 portions of methylene chloride and the combined extracts were dried over anhydrous magnesium sulfate and concentrated under reduced pressure to afford the nitrated N-acetyl derivative (approx. 175 g).

900 ml of 20% hydrochloric acid was added to this material and the suspension was stirred and refluxed for 9 hrs. Then the resulting solution was cooled and concentrated under reduced pressure to dryness. To ensure dryness, the residue was treated with 100 ml of absolute ethanol and concentrated to dryness. This operation was repeated twice more, then 300 ml of absolute ethanol was added and the mixture was stirred for 1 hr. Filtration and drying at 60° under reduced pressure gave 83.2 g of the hydrochloride of R(+)-α-methyl-p-nitrobenzylamine, m.p. 240°–242° dec. This product was purified further by refluxing it with 200 ml of absolute ethanol for 1 hr, cooling to 10°, and filtering, whereupon 76.4 g of purified product was obtained, m.p. 243°–245° dec. The free amine was recovered by addition of the hydrochloride to 450 ml of 1 N sodium hydroxide solution and extraction three times with 500 ml of methylene chloride. The extracts were dried over anhydrous magnesium sulfate and the solvent was removed by distillation under reduced pressure. Distillation of the residual oil gave 58.9 g of the pure amine, b.p. 119°–120°/0.5 mm, $[\alpha]_D^{24} = +16.5°$ (c = 3% in ethanol). The S(−)amine was prepared in identical fashion starting with s(−) α-methylbenzylamine.

EXAMPLE 2

38.85 g (200 mmoles) of racemic threo-epoxyaconitic acid dissolved in 250 ml of methanol-water (98:2 v/v) was treated with 59.80 g (360 mmoles) of R(+)-α-methyl-p-nitrobenzylamine in 150 ml of the same solvent. The warm solution immediately began to deposit solid and was left at room temperature overnight. The mixture set to a solid mass, which was mashed and filtered. The collected solid was rinsed with fresh solvent and dried in a vacuum oven at 45° overnight to give 50.5 g solid with $[\alpha]_{436}^{25} +13.07°$ (c = 2.035% in water), approx. 87.3% optically pure. The solid was stirred and refluxed gently as a slurry with 400 ml of the same solvent for 2 hr, then allowed to cool to room temperature with stirring ovenight to give 44.78 g of solid with $[\alpha]_{436}^{25} +14.83°$ (c = 2% in water). This salt contained 2 moles of amine per mole of acid and was 99.1% optically pure by comparison with an authentic sample prepared by reacting optically pure (+)-threo-epoxyaconitic acid with R(+)α-methyl-p-nitrobenzylamine.

EXAMPLE 3

9.12 g (48 mmoles) racemic threo-hydroxycitric acid γ-lactone was dissolved in 80 ml of ethanol and to this a solution of 10 g (60 mmoles) R-(+)-α-methyl-p-nitrobenzylamine in 20 ml methanol was added. The solution was stirred overnight and the resulting solids were filtered and washed with methanol to give 9.3 g of crude product $[\alpha]_D^{25} = +30.7°$. The crude salt was purified by refluxing in 100 ml ethanol for 3 hrs, then cooling the mixture and filtering the solid to give 7.56 g of pure salt $[\alpha]_D^{25} = +38.2°$. The salt contained 2 moles of amine per mole of acid.

9.7 g (18.6 mmole) of the above salt was suspended in 75 ml of diethyl ether and to this 50 ml of a 1 N ethereal hydrogen chloride solution was added. The mixture was stirred at room temperature for 20 minutes under anhydrous conditions. The solid was recovered by filtration and washed with ether to give 7.7 g of the hydrochloride of R-(+)- α-methyl-p-nitrobenzylamine, m.p. 245°–247°. The combined filtrates were concentrated in vacuo to give 3.35 g of lactone. This material was crystallized from ethyl acetate-CCl₄ to give 2.6 g of the γ-lactone of (−)- threo-hydroxycitric acid $[\alpha]_D^{25} = +106.1°$ (1% H₂O): m.p. 179°–180.5°. A second crop gave 0.33 g of lactone, m.p. 178°–180°, $[\alpha]_D^{25} +106.4°$.

EXAMPLE 4

65.7 g (0.122 mole) of the bis R-(+)-α-methyl-p-nitrobenzylamine salt of (+)-threo-epoxyaconitic acid (98–99% optical purity) and 73 ml of 0.5 N HCl (0.365 mole) were heated at reflux for 16 hrs. The solution was cooled and extracted with EtOAc (2 × 100 ml). The organic layers were backwashed in turn with water (50 ml) and the combined aqueous layers were evaporated to dryness under reduced pressure. The residue was triturated with EtOAc (3 × 100 ml) and the solids were recovered by filtration to give 44.8 g (91.4%) of recovered R(+)-α-methyl-p-nitrobenzylamine hydrochloride (m.p. 246°–7°). The filtrate was dried over MgSO₄, evaporated in vacuo and the residue was heated at 75°–80°in vacuo for ½ hr. to ensure lactonization. Crystallization of the residue (21 g) from EtOAc-CCl₄ furnished the γ-lactone of (−)-threo-hydroxycitric acid in two crops: 6.0 g [m.p. 174°–6°; $[\alpha]_D^{25} +$ 105.6° and 3.2 g [1⅓°–173°; $[\alpha]_D^{25} +100.5°$]. The crops were combined and recrystallized from EtOAc-CCl₄ (after decolorization using acid-washed Norit Sv charcoal) to give the γ-lactone in two crops; m.p. 178°–180°, $[\alpha]_D^{25} +106.2°$, and m.p. 178°–180°, $[\alpha]_D^{25} +105.9°$.

EXAMPLE 5 dl-N-formyl-6-chlorotryptophan 15 g(628 mM) of dl-6-chlorotryptophan was treated with 15 ml of acetic-formic anhydride. An exothermic reaction ensued, accompanied by solidification of the reaction slurry. Excess solvents were distilled off under vacuum and the resultant solids, after first leaching with dilute acid, were recrystallized from ethyl acetate to yield 12.45 g, 74%, of product, m.p. 181°–3° dec.

EXAMPLE 6

N-formyl-L-6-chlorotryptophan R-(+)α-methyl-p-nitrobenzylamine salt 12.45 g (46.7 mM) of dl-N-formyl-6-chlorotryptophan and 7.76 g of R-(+)- α-methyl-p-nitrobenzylamine were dissolved in 155 ml of acetone. The crude solids which separated out were recrystallized three times from ethanol to yield 1.94 g, product, m.p. 133°–4°, $[\alpha]_D^{22} = +23.0°$ (c=1, methanol).

EXAMPLE 7

N-formyl-L-6-chlorotryptophan hydrate 1.94 g (4.5 mM) of N-formyl-L-6-chlorotryptophan R(+)-α-methyl-p-nitrobenzylamine salt was slurried with 50 ml of 0.1 N HCl. The resultant solids were filtered off and crystallized from water-ethanol to yield 1.09 g of product, m.p. 143°–5°, $[\alpha]_D^{22} = +47.1°$ (c=1, methanol).

EXAMPLE 8

L-6-chlorotrypotophan 5.16 g (18.1 mM) of N-formyl-L-6-chlorotryptophan hydrate and 100 ml of 2 N acetic acid was refluxed for 22 hrs. The reaction mixture was concentrated in vacuo to solids which were leached with ethanol and crystallized from water to give 2.41 g of product, m.p. dec. with gas evolution 246°C, $[\alpha]_D^{22} = -15.4°$ (c=1, glacial acetic acid), $[\alpha]_D^{22} = -28.5°$ (c=1, methanol).

EXAMPLE 9

N-formyl-D-6-chlorotryptophan S-(−)-α-methyl-p-nitrobenzylamine salt

The acetone filtrate from which the crude product from Example 6 separated out was concentrated in vacuo to dryness. The resultant oil residue was suspended in water and the mixture was adjusted to pH 1 with dilute HCl and extracted with ethyl acetate. The ethyl acetate extracts were concentrated in vacuo to an oil and treated with dilute HCl to give 6.94 g of partially resolved chlorotryptophan, $[\alpha]_D^{22} = -18.9°$ (c=1, methanol). This material and 4.79 g of S(−)-α-methyl-p-nitrobenzylamine p-nitrobenzylamine were dissolved in 85 ml of acetone. The crude solids which separated out were recrystallized one time from methanol to yield 4.65 g of product, m.p. 183°–4°, $[\alpha]_D^{22} = -27.4°$ (c=1, MeOH).

EXAMPLE 10

N-formyl-D-6-chlorotryptophan 4.65 g (10.1 mM) of N-formyl-D-6-chlorotryptophan S(-31)-α-methyl-p-nitrobenzylamine salt was slurried with about 65 ml of 0.2 NHCl. The resultant solids were filtered off and crystallized from water-ethanol to yield 2.32 g of product, m.p. 143° –5°C, $[\alpha]_D22 = -47.0°$ (c=1, MeOH).

EXAMPLE 11

D-6-chlorotryptophan 1.06 g (5.82 mM) of N-formyl-D-6-chlorotryptophan and 34 ml of 2 N acetic acid was refluxed for 22 hrs. The reaction mixture was concentrated in vacuo to solids which were leached with a small amount of ethanol and crystallized from water to give 0.65 g of product, m.p. dec. with gas evolution 264°, $[\alpha]_D^{22} = +15.0°$ (c=1, glacial acetic acid), $[\alpha]_D^{22} 22 = +28.2°$ (c=1, MeOH).

EXAMPLE 12

Following the procedure of Example 6, but using S(−)-α-methyl-p-nitrobenzylamine as the initial resolving agent, there was obtained as a precipitate N-formyl-D-6-chlorotryptophan S(−)-α-methyl-p-nitrobenzylamine salt, m.p. 183°–4°, $[\alpha]_D^{22} + -27.4°$ (c=1, MeOH). The salt was decomposed, according to the procedure in Examples 7 and 10 to afford N-formyl-D-6-chlorotryptophan, m.p. 143°–5°, $[\alpha]_D^{22} = -47.0°$ (c=1, MeOH), which was deformylated according to the procedures in Examples 8 and 11 to afford D-6-chlorotryptophan, m.p. dec. 264°)$[\alpha]_D^{22} = +15.0°$ (c=1, glacial acetic acid), $[\alpha]_D^{22} = +28.2°$ (c=1, MeOH). From the filtrate following the initial precipitation there was obtained, after following the procedures in Examples 9-11, N-formyl-L-6-chlorotryptophan R(+)-α-methyl-p-nitrobenzylamine salt, N-formyl-6-chlorotryptophan hydrate, and N-formyl-6-chlorotryptophan, respectively.

We claim:
1. (+)-threo-Epoxyaconitic acid bis-R(+)-α-methyl-p-nitrobenzylamine salt.

* * * * *